United States Patent [19]

Pedrazzini et al.

[11] Patent Number: 5,817,912

[45] Date of Patent: Oct. 6, 1998

[54] TRANSGENIC MICE WITH DISRUPTED NPY Y1 RECEPTOR GENES

[75] Inventors: Thierry Pedrazzini, Morrens; Hans R. Brunner, Pully, both of Switzerland

[73] Assignee: B.M.R.A. Corporation B.V., Netherlands

[21] Appl. No.: 784,289

[22] Filed: Jan. 16, 1997

[51] Int. Cl.$^6$ .............................. C12N 5/00; C12N 15/00; A61K 49/00
[52] U.S. Cl. .................. 800/2; 800/DIG. 1; 800/DIG. 2; 424/9.2; 435/172.3; 435/320.1; 435/354
[58] Field of Search ................................... 800/2, DIG. 1, 800/DIG. 2; 935/55, 60, 62; 435/320.1, 354, 172.3; 424/9.2

[56] References Cited

U.S. PATENT DOCUMENTS

| | | | |
|---|---|---|---|
| 5,434,340 | 7/1995 | Krimpenfort et al. | 800/2 |
| 5,532,158 | 7/1996 | Suzuki et al. | 435/240.2 |
| 5,557,032 | 9/1996 | Mak | 800/2 |
| 5,569,742 | 10/1996 | Kirby et al. | 530/317 |
| 5,571,695 | 11/1996 | Selbie et al. | 435/69.1 |

OTHER PUBLICATIONS

Capecchi, "The New Mouse Genetics: Altering the Genome by Gene Targeting," *Trends in Genetics* 5:70–79 (1989).

Eva et al., "Molecular Cloning o f a Novel G Protein–Coupled Receptor that May Belong to the Neuropeptide Receptor Family," *FEBS Letters* 271:81–84 (1990).

Eva et al., "The Murine NPY–1 Receptor Gene: Structure and Delineation of Tissue–Specific Expression," *FEBS Letters* 314:285–288 (1992).

Herzog et al., "Genomic Organization, Localization, and Allelic Differences in the Gene for the Human Neuropeptide Y Y1 Receptor," *J. Biol. Chem.* 268:6703–6707 (1993).

Herzog et al., "Cloned Human Neuropeptide Y Receptor Couples to Two Different Second Messenger Systems," *Proc. Natl. Acad. Sci. USA* 89:5794–5798 (1992).

Larhammar et al., "Cloning and Functional Expression of a Human Neuropeptide Y/Peptide YY Receptor of the Y1 Type," *J. Biol. Chem.* 267:10935–10938 (1992).

Mansour et al., "Disruption of the Proto–Oncogene int–2 in Mouse Embryo–Derived Stem Cells: A General Strategy for Targeting Mutations to Non–Selectable Genes," *Nature* 336:348–352 (1988).

Wahlestedt et al., "Modulation of Anxiety and Neuropeptide Y–Y1 Receptors by Antisense Oligodeoxynucleotides," *Science* 259:528–531 (1993).

Wahlestedt et al., "Evidence for Different Pre–and Post–Junctional Receptors for Neuropeptide Y and Related Peptides," *Regulatory Peptides* 13:307–318 (1986).

*Primary Examiner*—Deborah Crouch
*Attorney, Agent, or Firm*—Vinson & Elkins L.L.P.; Michael A. Sanzo

[57] ABSTRACT

The present invention is directed to transgenic animals which have been engineered by homologous recombination to be deficient in the expression of the neuropeptide Y Y1 receptor. The invention encompasses the DNA constructs and engineered embryonic stem cells used to produce the animals, the transgenic animals themselves, and assays which utilize either the animals or tissues derived from the animals.

23 Claims, 9 Drawing Sheets

```
            10          20          30          40
             *           *           *           *
GAA TTC TCC ATT TCT GGC CTT TGA GAA TGA TGA CTG CCA CCT GCC 50          60          70          80          90
     *           *           *           *           *
CTT GGC TGT GAT ATT CAC CTT AGC TCT TGC TTA TGG GGC TGT GAT 100         110         120         130
             *           *           *           *
TAT TCT TGG GGT CTC TGG AAA CCT GGC ATT GAT CAT AAT CAT CCT 140         150         160         170         180
     *           *           *           *           *
AAA ACA GAA AGA GAT GAG GAA TGT CAC CAA CAT TCT GAT CGT GAA 190         200         210         220
             *           *           *           *
CCT CTC CTT CTC AGA CTT GCT GGT CGC AGT CAT GTG TCT CCC GTT 230         240         250         260         270
     *           *           *           *           *
CAC CTT TGT GTA CAC ACT GAT GGA CCA CTG GGT CTT CGG GGA GAC 280         290         300         310
             *           *           *           *
CAT GTG CAA ACT GAA TCC TTT TGT GCA ATG CGT CTC CAT TAC AGT 320         330         340         350         360
     *           *           *           *           *
ATC CAT TTT CTC TCT GGT TCT CAT CGC TGT GGA ACG TCA TCA GCT 370         380         390         400
             *           *           *           *
AAT CAT CAA CCC AAG AGG GTG GAG ACC AAA CAA TAG ACA TGC TTA 410         420         430         440         450
     *           *           *           *           *
CAT AGG CAT TAC TGT CAT TTG GGT ACT GGC GGT GGC TTC TTC TCT 460         470         480         490
             *           *           *           *
GCC CTT CGT GAT CTA TCA AAT TCT GAC TGA TGA GCC CTT CCA AAA
```

FIG.6A

```
        500         510         520         530         540
         *       *   *       *   *       *   *       *   *
        TGT ATC ACT TGC GGC GTT CAA GGA CAA GTA TGT ATG TTT TGA CAA 550         560         570         580
         *       *   *       *   *       *   *       *   *
        ATT CCC GTC AGA CTC TCA CAG GCT GTC TTA CAC GAC TCT TCT TCT

590
         *       *
        GGT GCT GCA G
```

FIG.6B

```
         10         20         30         40
          *          *          *          *
AAG CTT TCT GGC ANA AGC ATG CGA CTC AGA GCA TTT CTA ACT CAT 50         60         70         80         90
      *          *          *          *          *
ACT GCA CAG ACG CGT AGA TGC GTT TCT ACA CAG CGT GCT GCA TAG 100        110        120        130
          *          *          *          *
TAA CTA GTG TTA ACT CTC ACA TTA TCC TTC ACT GCA GAG ACA CAG 140        150        160        170        180
      *          *          *          *          *
GAC AAT GTC AAT GTA TCT ACC NTT CAG CTA ACA GAT GTC TGT ACC 190        200        210        220
          *          *          *          *
TAA ACT TCA CGC AGC CTA ACT TGT ATA AAC TGT ATA CAA GTT CAA 230        240        250        260        270
      *          *          *          *          *
GTT CAT CCT AAC TTG TAT AAA CTG TAT AAT GTG TGG AGT TTT ATA 280        290        300        310
          *          *          *          *
ATC ATA TAC TAT TAT ATC ATA GAG TAC TGA GTA GCC CTG CCA TAT 320        330        340        350        360
      *          *          *          *          *
TGA TAT ATT TAC TTT CAT GTA TCT TGT AAT CAT GAT TTA GAC TCA 370        380        390        400
          *          *          *          *
GAA AAG ATA CTT TGA AGA ACA AGA CAG TTT CAA TGT ATT GTA CAA 410        420        430        440        450
      *          *          *          *          *
ATG TTG CCT GTG TGT GAT TTT AGA AGG GCA GAC ACT TCT GAA TTA 460        470        480        490
          *          *          *          *
AAA CTG AGA CTT TTC AGA GGA GTC TGT TCT GTG ATT CTC TTG AGC
```

FIG.7A

```
       500         510         520         530         540
        *     *     *     *     *     *     *     *     *
       TTC   CTT   TCT   TCC   TGT   CTC   AAG   ACT   TGC   CTT   CCA   TGA   TAT   GAT   ACC 550         560         570         580
        *     *     *     *     *     *     *     *     *
       TCC   ACC   ATA   CCC   ATT   ACC   AAC   TGG   CTA   GAG   AGT   TAC   TGT   CTA   TTC 590         600         610         620
        *     *     *     *     *     *     *
       TGT   AAC   CAC   TGG   GGG   CTC   GTA   CAC   TTT   AAT   TTT   CTA   GA
```

FIG.7B

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 595 base pairs
( B ) TYPE: nucleic acid
( C ) STRANDEDNESS: double
( D ) TOPOLOGY: linear ( i i ) MOLECULE TYPE: cDNA ( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| GAATTCTCCA | TTTCTGGCCT | TTGAGAATGA | TGACTGCCAC | CTGCCCTTGG | CTGTGATATT | 6 0 |
| CACCTTAGCT | CTTGCTTATG | GGGCTGTGAT | TATTCTTGGG | GTCTCTGGAA | ACCTGGCATT | 1 2 0 |
| GATCATAATC | ATCCTAAAAC | AGAAAGAGAT | GAGGAATGTC | ACCAACATTC | TGATCGTGAA | 1 8 0 |
| CCTCTCCTTC | TCAGACTTGC | TGGTCGCAGT | CATGTGTCTC | CCGTTCACCT | TTGTGTACAC | 2 4 0 |
| ACTGATGGAC | CACTGGGTCT | TCGGGGAGAC | CATGTGCAAA | CTGAATCCTT | TTGTGCAATG | 3 0 0 |
| CGTCTCCATT | ACAGTATCCA | TTTTCTCTCT | GGTTCTCATC | GCTGTGGAAC | GTCATCAGCT | 3 6 0 |
| AATCATCAAC | CCAAGAGGGT | GGAGACCAAA | CAATAGACAT | GCTTACATAG | GCATTACTGT | 4 2 0 |
| CATTTGGGTA | CTGGCGGTGG | CTTCTTCTCT | GCCCTTCGTG | ATCTATCAAA | TTCTGACTGA | 4 8 0 |
| TGAGCCCTTC | CAAAATGTAT | CACTTGCGGC | GTTCAAGGAC | AAGTATGTAT | GTTTTGACAA | 5 4 0 |
| ATTCCCGTCA | GACTCTCACA | GGCTGTCTTA | CACGACTCTT | CTTCTGGTGC | TGCAG | 5 9 5 |

( 2 ) INFORMATION FOR SEQ ID NO:2:

( i ) SEQUENCE CHARACTERISTICS:
( A ) LENGTH: 623 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

| | | | | | | |
|---|---|---|---|---|---|---|
| AAGCTTTCTG | GCANAAGCAT | GCGACTCAGA | GCATTTCTAA | CTCATACTGC | ACAGACGCGT | 60 |
| AGATGCGTTT | CTACACAGCG | TGCTGCATAG | TAACTAGTGT | TAACTCTCAC | ATTATCCTTC | 120 |
| ACTGCAGAGA | CACAGGACAA | TGTCAATGTA | TCTACCNTTC | AGCTAACAGA | TGTCTGTACC | 180 |
| TAAACTTCAC | GCAGCCTAAC | TTGTATAAAC | TGTATACAAG | TTCAAGTTCA | TCCTAACTTG | 240 |
| TATAAACTGT | ATAATGTGTG | GAGTTTTATA | ATCATATACT | ATTATATCAT | AGAGTACTGA | 300 |
| GTAGCCCTGC | CATATTGATA | TATTTACTTT | CATGTATCTT | GTAATCATGA | TTTAGACTCA | 360 |
| GAAAAGATAC | TTTGAAGAAC | AAGACAGTTT | CAATGTATTG | TACAAATGTT | GCCTGTGTGT | 420 |
| GATTTTAGAA | GGGCAGACAC | TTCTGAATTA | AAACTGAGAC | TTTTCAGAGG | AGTCTGTTCT | 480 |
| GTGATTCTCT | TGAGCTTCCT | TTCTTCCTGT | CTCAAGACTT | GCCTTCCATG | ATATGATACC | 540 |
| TCCACCATAC | CCATTACCAA | CTGGCTAGAG | AGTTACTGTC | TATTCTGTAA | CCACTGGGGG | 600 |
| CTCGTACACT | TTAATTTTCT | AGA | | | | 623 |

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

AAATGTGTCA CTTGCGGCGT TC                      22

( 2 ) INFORMATION FOR SEQ ID NO:4:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

TGGCTATGGT CTCGTAGTCA TCGTC                 25

( 2 ) INFORMATION FOR SEQ ID NO:5:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO

-continued (iv) ANTI-SENSE: NO (xi) SEQUENCE DESCRIPTION: SEQ ID NO:5:

AAGCCCATCA CCATCTTCCA GGAG    24

(2) INFORMATION FOR SEQ ID NO:6:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

AGCCCTTCCA CAATGCCAAA G    21

TRANSGENIC MICE WITH DISRUPTED NPY Y1 RECEPTOR GENES

FIELD OF THE INVENTION

The present invention relates to transgenic animals engineered by homologous recombination to be deficient in the production of the Y1 receptor for neuropeptide Y. In addition, the invention encompasses the DNA constructs and embryonic stem cells used to develop the transgenic animals and assays which utilize either the animals or tissues derived from the animals.

BACKGROUND OF THE INVENTION

A. Physiology of Neuropentide Y

Neuropeptide Y (NPY) is a 36 amino acid peptide which belongs to a family of neuroendocrine peptides consisting of NPY, peptide YY (PYY) and pancreatic polypeptide (PP). It is widely distributed throughout the central and peripheral nervous systems of mammals (Grundemar, et al., *Gen. Pharmacol.* 24:785 (1993); McDermott, et al., *Cardiovasc. Res.* 27:893 (1993)). In the brain, NPY is particularly abundant in the hypothalamus, the limbic system and the cortex (Dimaggio, et al., *Neurosci.* 15:1149 (1985)). In the periphery, it is localized in sympathetic nerve fibers which surround blood vessels and other smooth muscle tissues.

NPY exerts a remarkably wide variety of physiological effects of potential therapeutic importance. It induces vasoconstriction when administered alone and acts synergistically when administered with other vasoconstrictors such as KC1, ATP, angiotensin II and histamine (Wahlestedt, et al., *Ann. NY Acad. Sci.* 611:7 (1990); Lundberg, et al., *Ann. NY Acad. Sci.* 611:166 (1990); Wahlestedt, et al., *Am. J. Physiol.* 258:R736 (1990); Oshita, et al., *Gen. Pharmacol.* 20:363 (1989)). When acting upon coronary arteries, the vasoconstrictive action of NPY can cause angina pectoris (Clarke, et al., *Lancet* 1 (8541):1057 (1987)). In addition, NPY has been found to restore the response to vasoconstrictors after desensitization which follows multiple exposure to vasoactive substances or after endotoxic shock (Hauser, et al., *Am. J. Physiol.* 265:H1416 (1993)).

NPY also exerts a mitogenic effect on aortic and venous smooth muscle tissue, and may contribute to cardiovascular hypertrophy in hypertension. Recent data suggests that it may promote angiogenesis as efficiently as basic fibroblast growth factor (Zukowska-Grojec, et al., *Peptides* 14:263 (1993)).

A third physiological action of NPY is in the hypothalamic regulation of body temperature, energy balance and metabolism. There is a large body of evidence indicating that NPY induces food intake in animals when injected in the hypothalamic area (Clark, et al., *Endocrinol.* 115:427 (1984); Stanley, et al., *Life Sci.* 35:2635 (1984); Levine, et al., *Peptides* 5:1025 (1984)). Recent reports suggest that it is the major mediator of the action of OB/leptin, a protein which acts centrally to reduce food consumption (Stephens, et al., *Nature* 377:530 (1995)), and that it has a direct anti-lipolytic effect on adipocytes (Castan, et al., *Am. J. Physiol.* 265:E74 (1993)).

Other results suggest that NPY may be important in the treatment of some forms of type II diabetes (Skoglund, et al., *Diabetes* 40:660 (1991); Opara, et al., *Regul. Peptides* 34:225 (1991)). Intracerebroventricular injection of the peptide enhances insulin secretion from pancreatic islets via autonomic control, whereas, in the periphery, NPY has a direct inhibitory effect on pancreatic insulin release.

Still another physiological effect reported for NPY is in the regulation of gonadotropin secretion. There are indications that it may play a role in follicular maturation and ovulation (Watanobe, et al., *Biochem. Biophys. Res. Comm.* 200:1111 (1994); Kalra, et al., *Ann. NY Acad. Sci.* 611:273 (1990); Jorgensen, et al., *Neuropep.* 30:293 (1996)). It has been found that NPY levels are elevated in rats with decreased sexual function and that ventral administration of the peptide reduces sexual performance. In addition, several lines of evidence indicate that sex steroids exert a feedback regulation on NPY levels (Sahu, et al., *Endocrinol.* 130:3331 (1992); Urban, et al., *Endocrinol.* 132:139 (1993)).

Reduced cortical concentrations of NPY have been observed in animal models of depression, and antidepressants have been found to increase NPY production (Widerlöv, et al., *Clin. Neurophannacol.* 9 (*Suppl.* 4):572 (1986)). NPY has been reported to produce an anxiolytic effect in animal models of anxiety (Heilig, et al., *Psychopharmacol.* 98:524 (1989)). In addition, concentrations of NPY are reduced in the CSF of patients with major depression or severe anxiety and in the brain tissue of some suicide victims (Widerlöv, et al., in *NPY*, V. Mutt et al. ed., pp. 331 Raven Press, NY (1989); Wahlestedt, et al., *Annu. Rev. Pharmacol. Toxicol.* 32:309 (1993)).

Other effects of NPY include: improved memory retention as observed in mice (Nakajima, et al., *J. Phannacol. Exp. Ther.* 268:1010 (1994)); analgesia in animal models of pain (Broqua, et al., *Brain Res.* 724:25 (1996)); inhibition of the excitatory amino acid glutamate, suggesting a possible role in epilepsy (Greber, et al., *Br. J. Phannacol.* 113:737 (1994)); and modulation of nasal vasodilation, rhinorrhea and bronchial secretion, suggesting possible importance in treating allergic rhinitis and cystic fibrosis (Lacroix, et al., *Br. J. Pharmacol.* 118:2079 (1996); Merten, et al., *Am. J. Physiol.* 266:L513 (1994)).

B. The Neuropeptide Y1 Receptor

At least six distinct subtypes of NPY receptors have been described and four subtypes have been cloned. The receptor subtypes, named Y1, Y2, etc., were initially classified based upon their selectivity for NPY, PYY and PP, as well as for their binding to NPY analogues and C-terminal fragments (see Table 1; Wahlestedt, et al., *Regul. Pept.* 13:307 (1986)).

TABLE 1

Characteristics of NPY Receptor Subtypes

| Receptor Subtype | Potency | Cloned |
| --- | --- | --- |
| Y1 | NPY = PYY = [Leu$^{31}$Pro$^{34}$]NPY >> NPY$_{13-36}$ | Yes |
| Y2 | NPY = PPY = NPY$_{13-36}$ >> [Leu$_{31}$Pro$_{34}$]NPY | Yes |
| Y3 | NPY = [Leu$_{31}$Pro$_{34}$]NPY = NPY$_{13-36}$ >> PYY | No |
| Y4("PP | PP >> PYY > NPY | Yes |

TABLE 1-continued

Characteristics of NPY Receptor Subtypes

| Receptor Subtype | Potency | Cloned |
|---|---|---|
| Preferring") | | |
| Y5 | $NPY_{2-36} \geq NPY = PYY = [Leu_{31}Pro_{34}]NPY \gg NPY_{13-36}$ | Yes |
| PYY Preferring | $PYY \gg NPY \gg NPY_{13-36} \gg [Leu_{31}Pro_{34}]NPY$ | No |

Y1 is the best characterized of the receptors for NPY, and has been cloned from the mouse (Eva, et al., *FEBS Lett.* 314:285 (1992)), rat (Eva, et al., *FEBS Lett.* 271:80 (1990)), and human (Larhammar, et al., *J. Biol. Chem.* 267:10935 (1992)). It is considered to be postsynaptic and mediates most of the actions of NPY in the periphery. Peripheral binding of NPY to Y1 receptors is believed to cause vasoconstriction and an increase in arterial blood pressure (Larhammar, et al., *J. Biol. Chem.* 267:10935 (1992); Westfall, et al., *Ann. NY Acad. Sci.* 611:145 (1990)). The Y1 receptor in the central nervous system has been associated with various effects of NPY, including the anxiolytic action of the peptide and a reduction of spontaneous locomotor activity (Wahlestedt, et al., *Science* 259:528 (1993)).

As with all of the NPY receptor subtypes, Y1 belongs to the G-protein coupled receptor family. The cloning, sequencing and expression of Y1 from different species has confirmed the presence of the seven transmembrane domains characteristic of G-protein coupled receptors and has revealed that the Y1 receptor gene is organized around two coding exons (exon 2 and exon 3), separated by a small intron (Herzog, et al., *J. Biol. Chem.* 268:6703 (1993); U.S. Pat. No. 5,571,695).

C. Gene Targeting Using Homologous Recombination

Gene targeting is a procedure in which foreign DNA sequences are introduced into a specific site within the genome of a host cell. Typically, a DNA construct is assembled in which sequences complementary to a gene of interest ("targeting sequences") are used to flank non-homologous elements. These constructs are introduced into cells by a variety of techniques, including electroporation. The constructs then enter into the nucleus of the cell where they anneal to genomic DNA. Due to a variety of factors not fully understood, "crossing over" sometimes occurs, which results in the homologous DNA sequences on annealed constructs replacing their counterparts within the host genome. When this occurs, the non-homologous DNA present in each recombining construct is carried along and also becomes part of the host genome. The introduction of the non-homologous DNA can be used to modify a chosen gene so that it can no longer express its normal product.

Although homologous recombination can result in the introduction of construct DNA into specific sites within a host genome, more typically, the DNA sequences are introduced at inappropriate sites. In order to differentiate homologous recombination from random genomic insertion, a strategy named "positive/negative selection" has been developed to enrich the cell population for cells in which recombination has occurred at the desired gene locus (Mansour, et al., *Nature* 336:348 (1988)). This is accomplished by engineering targeting vectors to contain an antibiotic resistance gene which, upon integration in the host cell genome, gives cells a selective advantage (positive selection). The vector also contains the Herpes simplex virus (HSV)-thymidine kinase (TK) gene adjacent to the homologous targeting sequences. When functionally integrated into the genome, HSV-TK makes a cell susceptible to the drug gancyclovir. The vector is designed so that when construct DNA integrates at the correct gene locus, the HSV-TK gene is not transferred into the genome. In contrast, a functional HSV-TK gene is incorporated into genomic DNA when integration occurs randomly. Thus, by incubating recombinants in the presence of gancyclovir, cells which have undergone random integration are selected against.

Recently, techniques have been developed for introducing the genomic variations resulting from homologous recombination into the germ cells of mice (for review, see Capecchi, *TIG* 5:70 (1989)). Embryonic stem (ES) cells are isolated from a developing mouse embryo at the blastocyst stage and used as a host for DNA constructs capable of introducing new sequences into genomic DNA by homologous recombination. When the modified ES cells are reintroduced into a blastocyst, they contribute to the formation of all tissues of the resultant chimeric animal, including the germ line (Bradley, et al., *Nature* 309:255 (1984)). By breeding chimeric animals and their heterozygous progeny, mice can be obtained which are homozygous for the mutation. Thus, it is possible to generate mice that are completely deficient for a given gene product.

D. Agents Binding to NPY Receptor Subtypes as Therapeutics

As discussed above, NPY is a peptide that mediates an exceptionally large number of physiological events, many of which have therapeutic significance. However, the diversity of NPY's actions make it unlikely that the peptide itself will be useful in the treatment of patients. Instead, new agents of greater specificity will need to be developed, and this will require an understanding of the specific actions mediated by each NPY receptor subtype.

The present inventors have utilized homologous recombination to develop cells and transgenic animals which contain mutations making them deficient in the expression of the Y1 receptor. Receptor-deficient cells and tissues derived from receptor-deficient transgenic animals may be used in binding assays along with their normal counterparts to evaluate the specificity of various NPY analogues and derivatives for the Y1 receptor subtype. Similarly, drugs may be administered directly to transgenic animals to determine if their physiological effects depend upon Y1 binding. Thus, the present invention provides a means for developing agonists and antagonists of NPY Y1 receptor binding as therapeutic agents.

SUMMARY OF THE INVENTION

The present invention is based upon the development of an animal model that can be used for evaluating drugs that act by modulating the binding of neuropeptide Y to the Y1 receptor. The invention includes not only the transgenic animals per se, but also the various materials used in the development of these animals, the specific methods by which they are formed and the assays in which they are used.

A. DNA Constructs

In its first aspect, the invention is directed to a DNA construct that can be used in the development of transgenic animals deficient in the production of NPY Y1 receptors. The construct must contain a targeting segment consisting essentially of the nucleotide sequence of an endogenous Y1 receptor gene within the genome of a host cell. A portion of the sequence of the targeting segment must be interrupted or replaced with a marker sequence not normally present in the endogenous Y1 receptor gene. Upon introduction into the host cell, the targeting segment must be capable of integrating into the genome at the site of the endogenous Y1 receptor gene. When this occurs, a mutant NPY Y1 receptor allele is produced that is incapable of synthesizing a fully functional Y1 receptor.

There are several features of the DNA constructs described above which deserve further comment. First, the essential feature of the targeting segment of the construct is that it must have a sequence sufficiently homologous with the sequence of the endogenous NPY Y1 receptor gene to undergo homologous recombination at the gene locus. However, the sequences need not be completely identical. Although any type of cell normally expressing the Y1 receptor can be used, mouse cells are preferred.

The marker sequence, which is used to interrupt or replace a portion of the targeting segment must result in a recombinant NPY Y1 sequence that has been sufficiently disrupted to result in a protein that is no longer fully functional. For example, the marker may disrupt the normal reading frame of the NPY Y1 receptor gene so that a protein is produced which cannot bind neuropeptide Y at all. Preferably, the marker sequence will be expressed in the host cell and form a product that can be used in helping to select cells that have undergone homologous recombination. For example, the neomycin resistance gene may be used as a marker.

The marker nucleotide sequence is said to "interrupt" the NPY Y1 receptor gene in instances where it has been inserted into the sequence so that all of the original NPY Y1 nucleotides are still present but are separated by the marker sequence. Replacement occurs in situations where a portion of the original NPY Y1 sequence is deleted and the marker sequence takes its place.

The term "fully functional NPY Y1 receptor" refers to a receptor with a substantially reduced affinity for neuropeptide Y. In most instances, it is expected, and generally preferred, that either no receptor is produced or that a receptor is produced which has completely lost its ability to bind neuropeptide Y.

In addition to "marker" sequences, DNA constructs may further contain a "selection sequence" that can be used to distinguish between cells in which recombination has occurred at the NPY Y1 locus and cells where recombination has occurred at other sites in the genome. The most preferred selection sequence comprises the HSV-thymidine kinase gene.

Finally, it should be noted that the invention is not limited to DNA constructs with fragments derived from any specific portion of the NPY Y1 receptor gene, nor is there a requirement that interruption or displacement of the gene by markers occur at a particular site. One DNA construct which has been demonstrated as effective spans exon 2 and exon 3 of the NPY Y1 receptor gene and uses the neomycin resistance gene to replace most of exon 2 and most of the intron between exons 2 and 3. In a preferred embodiment, this construct also contains the HSV-thymidine kinase gene as a selection sequence.

B. Host Cells Transformed with DNA Constructs

In addition to the DNA constructs described above, the present invention encompasses host cells comprising these constructs. Any type of cell normally expressing the NPY Y1 receptor may serve as host but, most preferably, the host will be a mouse embryonic stem cell.

C. Method of Making a Transgenic Mouse Deficient in NPY Y1 Receptors

In another aspect, the present invention is directed to a method of producing a transgenic mouse having a phenotype characterized by the substantial absence of NPY Y1 receptors. The first step in this method involves making a DNA construct according to the procedures set forth above. The construct contains a targeting segment which consists essentially of the nucleotide sequence of the mouse NPY Y1 receptor gene. A portion of the targeting fragment is modified by integrating or replacing it with a marker sequence not normally found in Y1. The fragment is constructed in such a manner that it is capable of integrating into the genome of a mouse ES cell at the site of the endogenous NPY Y1 gene and, when so incorporated, it produces a mutant NPY Y1 allele incapable of synthesizing fully functional receptors.

The next step in the method involves introducing the construct into mouse embryonic stem cells for the purpose of integrating the fragment into the mouse genome at the NPY Y1 receptor gene locus. The recombinant stem cells so produced are selected and then incorporated into a mouse blastocyst to form a chimeric embryo. This is implanted into a pseudopregnant mouse and allowed to develop into a viable offspring.

The offspring produced using the procedures described above, are screened to identify heterozygous mice containing a mutant NPY Y1 receptor gene allele. These mice are then bred to develop homozygous transgenic mice having a phenotype characterized by the substantial absence of filly functional NPY Y1 receptors.

In preparing the DNA construct for use in the above method, it is preferred that the marker sequence be comprised of the neomycin resistance gene and that the construct further contain the HSV-thymidine kinase gene. Although the marker may be inserted at any place in the NPY Y1 receptor gene sequence resulting in a non-functional gene product, it is preferred that the neomycin resistance gene be used to replace a portion of exon 2.

In addition to the method discussed above, the present invention is also directed to transgenic mice that are produced by the method. These mice should typically have no functional NPY Y1 receptors at all. However, the invention also includes mice in which receptors are either substantially reduced in terms of their number or which show a greatly decreased affinity for neuropeptide Y.

D. Transgenic Animals

In another aspect, the present invention is directed to a transgenic animal having a phenotype characterized by the substantial absence of NPY Y1 receptors otherwise naturally occurring in the animal. Preferably, the transgenic animal is produced using the methods described above, is a mouse and contains a transgene located at the NPY Y1 receptor gene locus in both its somatic and germ cells. In addition, the invention encompasses biological material obtained from the transgenic animals and consisting of cells, tissues or cell lines. These cells, tissues and cell lines are characterized by the substantial absence of NPY Y1 receptors otherwise naturally occurring in their normal counterparts.

E. Assay Methods Utilizing Transgenic Animals and Tissues Derived from Transgenic Animals The present invention is also directed to a method for conducting assays using transgenic animals that have been engineered to be deficient in the production of NPY Y1 receptors. One assay is designed to evaluate a drug to determine if it produces a physiological response in the absence of NPY Y1 receptors. This may be accomplished by administering the drug to a transgenic animal as discussed above, and then assaying the animal for a particular response. Although any physiological parameter could be measured in this assay, responses preferred include: a change in blood pressure; neovascularization; analgesia; a change in eating behavior; a change in body weight; a change in body temperature; insulin secretion; gonadotropin secretion; nasal and bronchial secretion; vasoconstriction; loss of memory; anxiety; pain or stress responses.

Tissues derived from transgenic animals may be used in receptor binding assays to determine whether test compounds bind to the NPY Y1 receptor. These assays can be conducted by obtaining a first receptor preparation from the transgenic animal engineered to be deficient in NPY Y1 receptor production and a second receptor preparation from a source known to bind neuropeptide Y. In general, it is expected that the first and second receptor preparations will be similar in all respects except for the source from which they are obtained. For example, if brain tissue from transgenic animals is used in an assay, it would be expected that comparable brain tissue from a normal mouse would also be used. After the receptor preparations are obtained, they may be incubated with a ligand known to bind to neuropeptide Y receptors both alone and in the presence of the test compound. Preferably, the test compound will be examined at several different concentrations.

The extent to which ligand binding is displaced by the test compound should be determined for both the first and second receptor preparations. Tissues derived from transgenic mice may be used in assays directly or the tissues may undergo a variety of procedures designed to isolate membranes or membrane proteins. The preferred transgenic animal is the mouse and the preferred ligand is detectably labeled neuropeptide Y. The ligand may be labeled using any means compatible with binding assays. This would include, without limitation, radioactive, enzymatic or chemiluminescent labeling.

F. Reducing Food Consumption by Administering a NPY Antagonist that Binds Specifically to the Y1 Receptor Subtype The development of transgenic animals as discussed above has led to the discovery that food consumption may be altered in response to the specific action of the Y1 receptor. Thus, the present invention is also directed to a method for reducing food consumption in a subject in need of restricting food intake by blocking the action of the NPY Y1 receptor subtype. This may be accomplished by administering an agent that antagonizes the action of NPY and which binds specifically to Y1.

The subject may be a human or any animal that normally makes NPY. An agent that "antagonizes the action of NPY" includes any compound that inhibits a physiological response normally induced in an animal by the administration of NPY. In general, a compound that binds to an NPY receptor but that fails to promote the action of adenyl cyclase in response to binding will be an antagonist. The phrase "binds specifically to Y1" refers to agents that bind to the Y1 receptor subtype to the exclusion of the other NPY receptor subtypes. Thus, a specific binder would be expected to have an affinity for Y1 that is at least a hundred times greater than for Y2, Y3 etc. Reduction is measured relative to the amount of food consumed in the absence of the NPY antagonist and may be evidenced by a significant ($p \leq 0.05$) reduction in the quantity of food ingested over a period of time (e.g. a week) and/or in a significant reduction in body weight. The Y1-specific antagonist of NPY should be administered in an amount and for a duration sufficient to reduce food consumption as reflected in one of these ways.

BRIEF DESCRIPTION OF THE DRAWINGS

FIG. 1 depicts a portion of the mouse NPY Y1 receptor allele which was involved in homologous recombination and the targeting segment used for disrupting the allele. A neomycin resistance gene has been incorporated as a marker in the targeting segment between two EcoRI sites, the first in exon 2 and the second in the following intron. The targeting vector also contains an HSV-thymidine kinase gene inserted downstream of exon 3 at a Hind III. site. Also shown in the figure is the recombined allele which results from homologous recombination between the targeting vector and wild type allele. Finally, the location of a probe used to identify DNA fragments in subsequent experiments is depicted.

FIG. 4 shows the results of a competitive binding assay performed using brain tissue membrane preparations derived from either wild type mice (WT) or mice homozygous for the NPY Y1 receptor mutation (KO). The binding of a constant amount of radioactively labeled NPY was measured in the presence of increasing concentrations of either unlabeled NPY or unlabeled BIBP, a Y1 specific analog of NPY. Unlabeled NPY displaced labeled NPY bound to the membranes of both wild type and KO mice. This is expected since the unlabeled NPY is able to compete for binding to all types of NPY receptors present on membranes. In contrast, unlabeled BIBP is only able to compete for the Y1 receptor subtype and, as a result, it shows a significantly reduced ability to displace labeled NPY from the membranes of wild type animals. The unlabeled BIBP showed no significant displacement of labeled NPY in membranes from KO mice indicating the absence of the NPY Y1 receptor.

FIG. 5 shows the effect of administering NPY on blood pressure in wild type mice (open bars), mice heterozygous for the NPY Y1 mutation (shaded bars), and mice homozygous for the NPY Y1 receptor mutation (black bars). Changes in blood pressure were determined by means of a catheter inserted in the carotid artery of mice and connected to a pressure transducer. NPY was administered to animals at concentrations of 0.24 μg/Kg, 1.2 μg/Kg, 6 μg/Kg and 30 μg/Kg by means of a separate catheter inserted into the jugular vein of the mice. The results suggest that the physiological increase in blood pressure caused by the administration of NPY is due to its binding to the Y1 receptor subtype.

FIG. 6: The nucleotide sequence of a portion of the rat NPY Y1 receptor gene is shown. This sequence was used as a probe in the screening of a mouse genomic DNA library for phage containing Y1 as described in Example 1. The sequence has been given the designation SEQ ID NO: 1.

FIG. 7: The figure presents the nucleotide sequence of the Hind III/Xba I probe shown in FIG. 1. This probe was used in experiments described in Example 2 and has been designated as SEQ ID NO:2.

FIG. 8 shows the results of a study in which food consumption was compared in starved wild type mice (open bar, (+/+)) and in starved NPY Y1 receptor-deficient mice (solid bar, (−/−)). Animals were deprived of food for 24 hours and then given a pre-weighed amount. Ninety minutes thereafter, the food was again weighed to determine the amount consumed. Results are expressed as the amount of food consumed over the 90 n minute test period normalized to body weight.

DETAILED DESCRIPTION OF THE INVENTION

Figure 1:
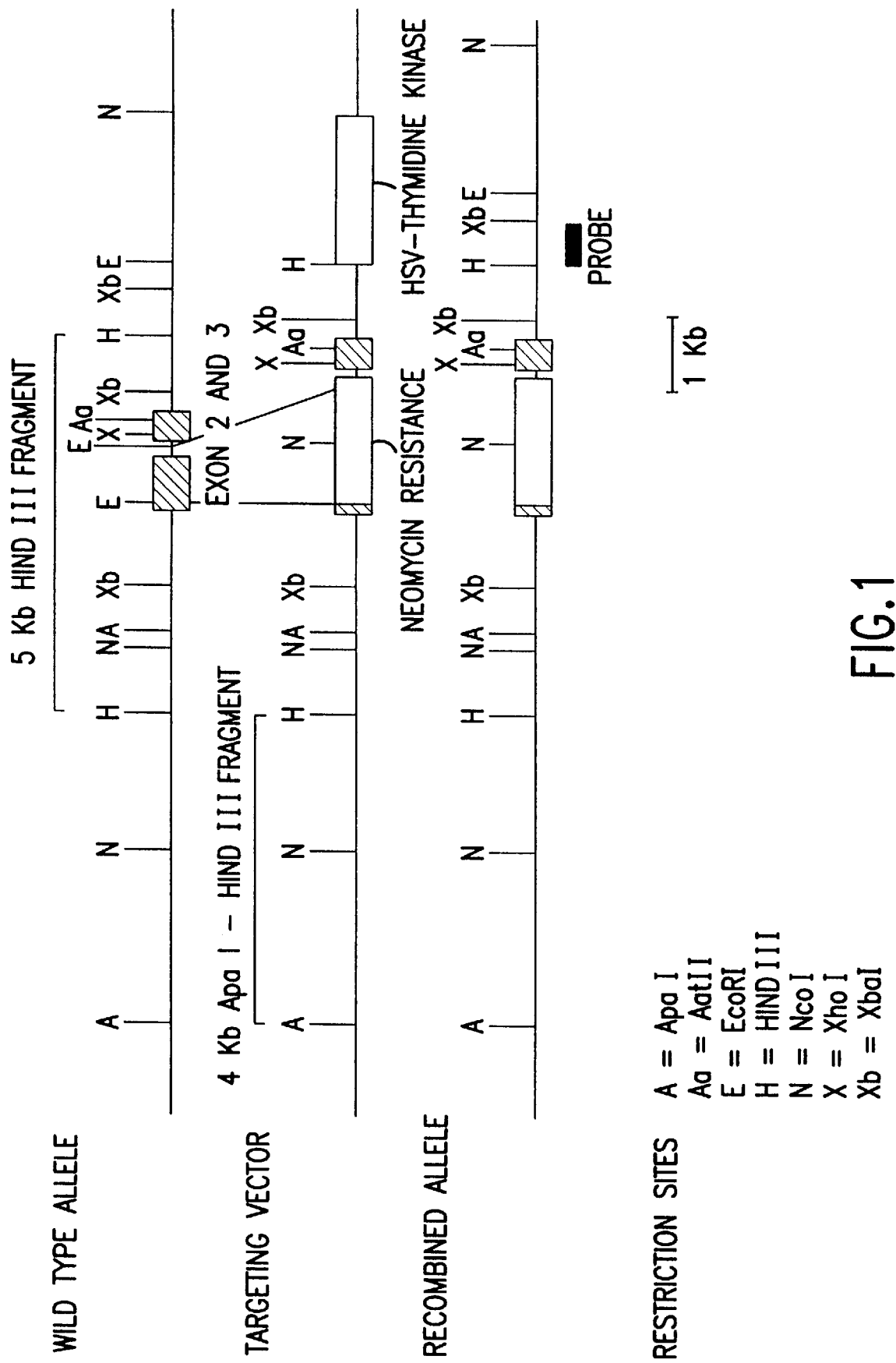
FIG. 1.

The present invention is directed to DNA constructs that can be used to disrupt an endogenous NPY Y1 receptor gene; to the recombinant cells, particularly recombinant embryonic stem cells, produced by incorporation of the DNA constructs; and to the method by which the recombinant cells are produced. Embryonic stem cells which have been engineered to contain a disrupted Y1 receptor allele can be incorporated into a developing embryo and, ultimately, used to produce transgenic mice which are deficient in the NPY Y1 receptor. Assays utilizing such mice may be performed for the purpose of evaluating drugs with potential use in the treatment of conditions mediated by the binding of neuropeptide Y. Both the transgenic mice per se and the assays in which they are used are also part of the invention.

A. DNA Constructs

The DNA constructs of the present invention are often referred to in the literature as "knockout" constructs because of their use in disrupting normally active genes. Typically, they contain a relatively long (>1 Kb) targeting segment that has a sequence highly homologous to an endogenous gene in a host cell and that is disrupted by a non-homologous marker sequence. The targeting segment used in constructs may be derived from either genomic or cDNA molecules by standard methods well known in the art (see, e.g., Sambrook, et al., *Molecular Cloning: A Laboratory Manual,* Cold Spring Harbor Laboratory Press, Cold Spring Harbor, N.Y. (1989)). For example, a portion of the NPY Y1 receptor gene may be isolated using PCR amplification based upon its known sequence or, as described in the examples herein, by screening a genomic library with an appropriate probe. Alternatively, the targeting segment in a construct may be made using chemical synthesis methods.

In order to incorporate a marker sequence, the targeting segment can be digested with one or more restriction enzymes selected to cut at specific locations. Any location which results in sufficient disruption of the NPY Y1 receptor gene to result in the elimination of a functional gene product after homologous recombination will suffice. Thus, disruption may take place either within the structural sequence of the receptor or at a regulatory element, e.g., the promoter, of the NPY Y1 receptor gene.

The marker sequence used in constructs will typically be an antibiotic resistance gene or other gene whose expression can be easily detected and which is not normally present in the host. The marker gene may be expressed in the host cell either as a result of its being operably linked to a promoter in the construct, or by coming under the control of the native NPY Y1 receptor gene promoter as a result of homologous recombination. In cases where it is part of the construct, the promoter should be selected based upon its having a high activity in the particular host cell undergoing homologous recombination. A typical example of a promoter suitable for use in mouse cells is the promoter of the phosphoglycerate kinase gene (used to induce expression of the Neomycin resistance gene in the construct of Example 1). The most preferred gene for use as a marker is the neomycin resistance gene (Neo). Cells which have integrated Neo into their genome and which are expressing this gene are resistant to G418. Thus, a simple means is provided for selecting recombinant cells. In addition to a promoter, the marker gene will typically have a polyA sequence attached to its 3' end.

In addition to a marker gene used for disrupting the NPY Y1 receptor and for identifying cells that have undergone homologous recombination, the constructs of the present invention will typically include a gene that can be used for distinguishing between cells in which recombination has occurred at the NPY Y1 receptor locus and cells in which recombination has occurred elsewhere in the genome. Preferably, this "selection sequence" will consist of the HSV-thymidine kinase gene under the control of an appropriate promoter. The combination of a marker sequence for selecting all cells that have undergone homologous recombination and a selection sequence for distinguishing site specific integration from random integration has been termed "positive-negative selection" and details of both the procedure and the production of constructs appropriate for the procedure are well known in the art (see Capecchi, M. *TIG* 5:70 (1989); Mansour, et al., *Nature* 336:348 (1988); Thomas, et al., *Sell* 51:503 (1987); and Doetschman, et al., *Nature* 330:576 (1987)).

The DNA construct for disruption of the NPY Y1 receptor gene may be transfected directly into appropriate host cells or it may first be placed in a vector for amplification prior to transfection. Preferred vectors are those that are rapidly amplified in bacterial cells such as the pBluescript IISK vector (Stratagene, San Diego, Calif.) or pGEM 7 (Promega Corp., Madison, Wis.).

DNA constructs may be either circular or linear. However, it is generally preferred that prior to transfection into host cells, circular constructs be linearized. Although any NPY Y1 receptor gene may be used in the making of DNA constructs, sequences homologous to the receptor gene from mouse are generally preferred.

B. Production of Host Cells Comprising DNA Constructs

The present invention encompasses cells which have been genetically engineered using the DNA constructs described above. Any type of cell that normally expresses the NPY Y1 receptor gene may be used as a host. This includes without limitation, cells from humans, rats, hamsters, mice, etc. As discussed further below, the most preferred host cells are mouse embryonic stem (ES) cells.

In the case where it is desired to produce transgenic mice deficient in the NPY Y1 receptor, ES cells should be selected based upon their ability to integrate into and become part of the germ line of a developing embryo. Any ES cell line that has this characteristic may be used, e.g., the murine cell line D3 (ATCC, 12301 Parklawn Drive, Rockville, Md., Catalog No. CRL1934). After appropriate host cells have been chosen, they are cultured and prepared for DNA insertion using methods well-known in the art (see, e.g., Robertson, *In Teratocarcinomas and Embryonic Stem Cells: A Practical Approach,* E. J. Robertson, ed, IRL Press, Washington, D.C. (1987); Bradley, et al., *Current Topics in Devel. Biol.* 20:357–371 (1986); and Hogan, et al., *Manipulating the Mouse Embryo: A Laboratory Manual,* Cold Spring Harbor Laboratory Press, Cold Spring Harbor, N.Y. (1986)).

The introduction of NPY Y1 constructs into host cells can be accomplished using any of a variety of methods such as electroporation, microinjection or calcium phosphate treatment. In the case of embryonic stem cells, the preferred method of insertion is electroporation. If the DNA construct has been inserted into a vector, it is preferred that the DNA be linearized prior to transfection. Linearization can be accomplished by digesting the DNA vector with a restriction endonuclease selected to cut outside of the NPY Y1 construct sequence.

The screening of transfected cells can be carried out using several different methods. In cases where an antibiotic resistance gene has been used as a marker, cells can be cultured in the presence of antibiotic to identify recombinants. In cases where other types of markers are used, Southern hybridizations may be carried out using labeled probes specific for the marker sequence. Finally, if the marker gene encodes an enzyme whose activity can be detected (e.g., beta-galactosidase), enzymatic assays may be performed.

It will usually be desirable not only to identify cells in which recombination has occurred, but also to distinguish specific recombination, i.e., integration at the NPY Y1 receptor gene locus, from random insertion events occurring elsewhere in the genome. To identify cells with proper integration, chromosomal DNA can be extracted from cells using standard methods and Southern hybridizations can be performed using probes designed to hybridize specifically DNA derived from constructs. Alternatively, PCR amplification can be performed using primers that will only act in cells where homologous recombination has occurred at the receptor locus or which will produce a distinctive product of known size from such cells.

One way to enrich preparations for recombinants modified at the Y1 receptor locus is to incorporate the HSV-thymidine kinase gene into constructs at a position adjacent to the targeting segment. The construct is designed so that the HSV-tk gene is only transferred to the host cell genome when recombination occurs at the Y1 receptor gene site. Because the HSV-tk gene makes cells susceptible to the drug gancyclovir, the exposure of recombinants to this drug will negatively select against cells in which random integration has occurred (see Mansour, et al., *Nature* 336:348 (1988)).

It will be appreciated that homologous recombination will result in the disruption of one Y1 receptor allele much more frequently than in the disruption of both alleles. If one desires to produce cells that are completely deficient in the NPY Y1 receptor, it may therefore be necessary to conduct a second round of homologous recombination on cells that have already been selected as having one allele disrupted. In the second round of transfection, a marker should be used that is different from the marker used in producing the initial recombinants. For example, if a neomycin resistance gene was used to produce cells with one disrupted allele, beta-galactosidase may be used as a marker in the second construct. Screening for cells that have incorporated DNA at the Y1 receptor site may be carried out as described above. Ultimately, the disruption of both alleles of the NPY Y1 receptor gene should be reflected in a loss in the binding of labeled neuropeptide Y to cell membranes.

C. Development of Transgenic Animals Characterized by a Substantial Absence of Fully Functional NPY Y1 Receptors Embryonic stem cells engineered to contain a mutant NPY Y1 allele and produced by homologous recombination as described above, may be used to make transgenic animals with a substantial absence of functional Y1 receptors. These animals are characterized by a loss in the ability to bind ligands specific for Y1 and/or by a loss in expression from the Y1 gene locus. Preferably, the animals produce no functional Y1 receptors at all. The methodology needed to make such animals can be adapted to any non-human animal such as hamsters, rats or, preferably, mice.

The first step in the making of transgenic animals is to produce ES cells modified by homologous recombination to contain a mutant NPY Y1 receptor gene allele. This may be accomplished using the procedures described above.

The next step is to incorporate the mutant embryonic stem cells into an embryo. The preferred method for accomplishing this is by microinjection into an embryo at the blastocyst stage of development. In mice, blastocysts at about 3.5 days of development may be obtain by perfusing the uterus of pregnant animals (Bradley, in: *Teratocarcinomas and Embryonic Stem Cells: A Practical Approach,* Robertson, E. D., IRLP Press, Washington, D.C. (1987)). Preferred blastocysts are male and have genes coding for a coat color or other phenotypic marker that is different from the corresponding marker encoded by the stem cell genes. In this way, offspring are produced that can be easily screened for the presence of mutant NPY Y1 receptor alleles. For example, if the ES cell line carries the gene for a white coat, the embryo selected will, preferably, carry the gene for a black or brown coat and offspring carrying a mutant Y1 allele should have mosaic coats.

After the embryonic stem cells have been incorporated into the blastocyst, the chimeric embryo is implanted into the uterus of a pseudopregnant animal. Such animals may be prepared by mating females with vasectomized males of the same species. The pseudopregnant stage of the female is important for successful implantation and will vary from species to species. For mice, females about two to three days pseudopregnant should typically be used.

After chimeric embryos have been implanted into pseudopregnant animals, they are allowed to develop to term and offspring are then screened for the presence of a mutant NPY Y1 receptor allele. In cases where a phenotype selection strategy has been employed, e.g., based upon coat color as described above, initial screening may be accomplished by simple inspection of animals for mosaic coat color or some other readily apparent phenotypic marker. In addition, or as an alternative, chromosomal DNA may be obtained from the tissue of offspring, e.g., from the tail tissue of mice, and screened for the presence of a modified nucleotide sequence at the NPY Y1 receptor gene locus using Southern blots and/or PCR amplification.

Once offspring have been identified carrying the NPY Y1 receptor gene mutation, they can be interbred to produce homozygous animals characterized by an impaired synthesis of functional NPY Y1 receptors. Heterozygotes may be identified using Southern blots or PCR amplification as described above. Homozygotes may be identified by Southern blotting of equivalent amounts of genomic DNA obtained from the offspring of crossed heterozygotes, from the heterozygotes themselves, and from wild-type animals. Probes should be designed to bind to a portion of the NPY Y1 gene sequence present in all animals and the presence of mutant alleles can be determined by the relative position of bands in autoradiographs (for an example, see FIG. 2). Alternatively, analysis may be performed based upon the relative sizes of PCR amplification products or by performing binding assays using tissues known to normally express the NPY Y1 receptor.

Other means for identifying and characterizing transgenic animals are also available. For example, Northern blots can be used to probe mRNA obtained from tissues of offspring animals for the presence or absence of transcripts encoding either the NPY Y1 receptor, the marker gene, or both. In addition, Western blots might be used to assess NPY Y1 receptor expression by probing with antibody specific for the receptor.

Once homozygous transgenic animals have been identified, they may be interbred to provide a continual supply of animals that can be used in identifying pathologies dependent upon the presence of a functional NPY Y1 receptor and in evaluating drugs in the assays described below. In addition, these animals can provide a source of cells, tissues and cell lines that differ from the corresponding cells, tissues and cell lines from normal animals by the absence of fully functional NPY Y1 receptors.

D. Assay Methods Utilizing Transgenic Animals and Biological Material Derived From Transgenic Animals Transgenic animals deficient in the NPY Y1 receptor subtype can help in the development of new therapeutic agents in several ways. First, the animals can be used to identify receptor subtypes that are needed for the treatment of a particular condition. For example, suppose that a neuropeptide Y analog or derivative is found to both increase body weight in normal animals and to increase blood pressure. By administering the drug to NPY Y1 receptor-deficient animals, it can be determined whether either of these physiological effects depend upon binding to the NPY Y1 receptor. If an undesirable characteristic, e.g., increased blood pressure, is found to be associated with NPY Y1 receptor binding, then a reasonable strategy for drug development would be to either further modify the drug to eliminate Y1 receptor binding, or to co-administer the drug together with an antagonist specific for the Y1 receptor.

Typically, assays designed to evaluate the physiological effects of drugs and to arrive at drug development strategies based upon receptor specificity, will involve utilizing both normal and receptor deficient animals divided into a variety of experimental groups. For example, both normal and receptor-efficient animals may be placed in treatment and control groups. The drug treatment groups would receive whatever compound was being tested whereas the control groups would not.

Assays themselves may be carried out by selecting one or more particular physiological characteristics for examination, administering the desired agent to the treatment and control groups, and then evaluating the results observed. In general, it is desirable to use sufficient animals in each group to assure that statistically significant results can be obtained. Among the various biological characteristics that may be examined are: blood pressure (useful in evaluating treatments for hypertension and cardiovascular disorders); neovascularization and angiogenesis (useful in evaluating drugs that promote wound healing or inhibit tumor growth); pain sensitivity (useful in the development of analgesics or anesthetics); eating behavior (useful in the development of drugs for treating anorexia, bulimia, obesity or type II diabetes); changes in body temperature, energy balance and metabolism (useful in the development of drugs for treating conditions associated with abnormal hormonal secretion); insulin secretion (useful in the development of drugs for diabetes); gonadotropin secretion (useful in the development of drugs for infertility or sexual dysfunction); bronchial secretion (useful in the evaluation of drugs for cystic fibrosis); nasal vasodilation and rhinorrhea (useful in the development of drugs for allergic rhinitis); loss of memory (useful in the development of drugs for Alzheimer's disease); anxiety and stress (useful in the development of antidepressants); and vasoconstriction (useful in the development of cardiovascular agents). Among the parameters that may be varied are duration of drug delivery, dosage, route of administration or dosage form. It may also be desirable to test combinations of agents or to test animals at various ages or physiological states, e.g., animals that are overweight.

It is expected that drugs for testing in normal and NPY Y1 receptor-deficient animals will often be chosen based upon their binding characteristics. For example, drugs that bind to neuropeptide Y receptors in in vitro binding assays might be considered good candidates for testing and transgenic animals (for a description of a preferred NPY Y1 binding assay, see Martel, et al., *Mol. Pharmacol.* 38:494 (1990)). Many methods for performing binding assays have been described in the art (see e.g., Chard, "An Introduction to Radioimmune Assay and Related Techniques," in: *Laboratory Techniques in Biochemistry and Molecular Biology,* North Holland Publishing Company, N.Y. (1978); *Radioimmune Assay Method,* Kirkham, et al., ED., E&S Livingstone, Edinburgh (1970); Wang, et al., *Proc. Natl. Acad. Sci. USA* 90:10230–10234 (1993); and Rudolf, et al., *Eur. J. Pharmacol.* 271:R11 (1994)). Typically, receptor preparations are incubated with a ligand specific to receptors for neuropeptide Y and with a preparation of test compound. After binding is complete, the receptor is separated from the solution containing ligand and test compound, e.g., by filtration, and the amount of binding that has occurred is determined.

Preferably the ligand used in binding assays is neuropeptide Y detectably labeled with a radioisotope. However, fluorescent, enzymatic, or chemiluminescent labels can be used as well. Among the most commonly used fluorescent labeling compounds are fluorescein, isothiocyanate, rhodamine, phycoerythrin, phycocycanin, allophycocyanin, o-phthaldehyde and fluorescamine. Useful chemiluminescent compounds include luminol, isoluminol, theromatic acridinium ester, imidazole, acridinium salt, and oxalate ester. The most commonly used isotope is radioactive iodine.

Nonspecific binding may be determined by carrying out the binding reaction in the presence of a large excess of unlabeled ligand. For example, labeled neuropeptide Y may be incubated with receptor and test compound in the presence of a thousandfold excess of unlabeled neuropeptide Y. Nonspecific binding should be subtracted from total binding, i.e., binding in the absence of unlabeled ligand, to arrive at the specific binding for each sample tested. Other steps such as washing, stirring, shaking, filtering and the like may be included in the assays as necessary. Typically, wash steps are included after the separation of receptor-ligand complexes from ligand remaining in solution and prior to quantitation of the amount of ligand bound, e.g., by counting radioactive isotope. Specific binding obtained in the presence of test compound, preferably at several concentrations, is compared with that obtained in the presence of labeled ligand alone to determine the extent to which test compound has displaced ligand.

In performing binding assays, care must be taken to avoid artifacts which may make it appear that a test compound is interacting with a receptor or neuropeptide Y when, in fact, binding is being inhibited by some other mechanism. For example, the compound being tested should be in a buffer which does not itself substantially inhibit the binding of ligand to receptor. Preparations of test compound should also be examined for proteolytic activity and it is desirable that antiproteases be included in assays. Finally, it is desirable that compounds identified as displacing the binding of ligand to receptor be re-examined in a concentration range sufficient to perform a Scatchard analysis on the results. This type of analysis is well known in the art and can be used for determining the affinity of a test compound for receptor (see e.g., Ausubel, et al., *Current Protocols in Molecular Biology*, 11.2.1–11.2.19 (1993); *Laboratory Techniques in Biochemistry and Molecular Biology*, Work, et al., ED., M.Y. (1978), etc.). Computer programs may be used to help in the analysis of results (see, e.g., Manson, *Methods Enzymol.* 92:543–577 (1983); McPherson, "Kinetic, EBDA Ligand Lowry—A Collection of Radioligand Binding Analysis Programs," Elsevier-Biosoft, U.K. (1985)).

Assays for determining changes in a second messenger, e.g., changes in intracellular calcium concentration or adenyl cyclase activity, may be performed using compounds that have been identified as a result of their ability to bind to NPY Y1 receptors. Both of these types of assays are well known in the art (see e.g., Serradeil-Le Gal, et al., *FEBS Lett.* 362:192 (1995); Nakamura, et al., *Biochem. Biophys. Acta* 1284:134 (1996)).

By comparing results obtained using either cells, tissues or cell lines engineered to be deficient in the expression of NPY Y1 receptors with comparable non-transgenic cells or tissues, it can be determined whether a particular ligand is binding with specificity to the Y1 receptor subtype. For example, if it is observed that specific binding to receptor preparations of normal cells is the same as specific binding to the NPY Y1 deficient cells, this suggests that Y1 receptors are not playing a significant role in the specific binding observed. In contrast, if binding is greatly reduced or absent in the engineered preparation compared to the normal preparation, this suggests that interaction with the Y1 receptor is playing a substantial role in the observed specific binding. Ligands that are completely specific for the Y1 receptor should evidence no significant specific binding to Y1 deficient preparations at all.

It will be appreciated that animals deficient in the expression of the Y1 receptor subtype, and biological materials such as cells, tissues and cell lines derived from these animals, are also especially useful in the screening of compounds that bind to other types of NPY receptor subtypes (Y2, Y3 etc.). For example, if one were attempting to develop a drug specific for the Y2 receptor, transgenic mice deficient in the Y1 receptor could be used to establish that the drug was capable of producing its effect without binding to Y1. Cells or tissues obtained from the animals could be used in binding assays to directly determine the extent to which the drug bound to Y1.

E. Regulating Food Intake by Administering Agents that Bind with Specificity to the Y1 Receptor Subtype The production of transgenic mice deficient in the expression of the NPY Y1 receptor subtype and the use of such mice in assays examining the effect of Y1 on food consumption (see Example 7) has led to the development of a method for reducing food intake in subjects. This is accomplished by administering an agent that antagonizes the action of NPY and that binds specifically to the Y1 receptor subtype. Specificity for the Y1 receptor subtype can be determined using the binding assays discussed above. A compound specific for Y1 would be expected to significantly block the binding of labeled NPY to normal cells but to have no effect on the binding to similar cells from receptor-deficient mutants. If the agent itself were labeled, it would be expected to bind with specificity to normal cells but to evidence little or no specific binding to mutant cells.

An antagonist of NPY, in this context, means an agent that blocks a biological effect of NPY by competing for NPY-specific receptors but failing to induce the biological response normally generated as a result of receptor occupancy. One way to examine whether an agent binding to Y1 receptors is acting in an antagonistic manner is to determine whether receptor binding is accompanied by an increase in adenyl cyclase activity (see discussion above). Alternatively, the physiological effect of a Y1-specific binder can be determined directly by administering the agent to mice and examining its effect on food consumption.

The total daily dosage of Y1 specific NPY antagonist administered to a subject should be at least the amount necessary to significantly reduce food intake. A relatively small dosage of the agent may be given initially and then adjusted upward as it becomes clear that the subject can tolerate the treatment. Dosages may be provided in either a single or multiple dosage regiment. The optimal daily dose will be determined by methods known in the art and will be influenced by a variety factors such as the age and health of the subject.

The method is not limited to any particular dosage form or route of administration. Oral administration will generally be most convenient and is preferred provided the agent in question is capable of maintaining its ability to bind specifically to the Y1 receptor when delivered in this manner.

Having now described the invention, the same will be more readily understood through reference to the following Examples which are provided by way of illustration and which are not intended to limit the scope of the invention.

EXAMPLES

Example 1: Making of a DNA Construct Suitable for Disruption of the Mouse NPY Y1 Receptor Gene by Homologous Recombination A mouse genomic DNA library was screened by hybridization using a probe (see SEQ ID NO: 1) spanning the second exon of the rat NPY Y1 receptor gene in order to identify phage vectors containing the mouse NPY Y1 gene. Southern blot analysis of the phage DNAs, following incubation with various restriction enzymes, allowed the creation of a partial restriction map of the mouse NPY Y1 receptor gene in the region of the second and third exons. To create the targeting vector, a 5 Kb Hind III fragment was subcloned into a Hind III site of a pBluescript II plasmid vector (pBS). Sequencing of the coding region confirmed that the fragment contained the mouse NPY Y1 receptor gene.

Two EcoRI sites, separated by approximately 0.8 Kb, are present in the 5 Kb Hind III fragment, one in exon 2 and one in the following intron. The pBS vector also contains an EcoR1 site in its multiple cloning sites. In order to facilitate the insertion of the neomycin resistance gene between the two EcoR1 sites present in the Y1 gene, the EcoR1 site of the pBS vector was inactivated by point mutation. Most of the second exon was then removed following EcoR1 digestion, and the neomycin resistance gene was inserted by blunt ligation.

The complete Hind III fragment, containing the neomycin resistance gene, was excised from the pBS vector following Hind III digestion, and inserted into the unique Hind III site of the pIC19R/MC1-TK plasmid (pIC), which contains the HSV-thymidine kinase gene. In order to extend the 5' homologous region, a 5.3 Kb Apa I fragment, overlapping with the 5 Kb Hind III described above and spanning the 5' region of the NPY Y1 receptor gene immediately adjacent, was subcloned into the Apa I site of pBS. A bacterial selection cassette conferring chloramphenicol resistance was inserted into the Cla I site of this vector. Then, following Hind III digestion, a fragment was isolated containing the chloramphenicol resistance gene and the region of the mouse Y1 gene extending from the 5' Hind III site of the 5 Kb Hind III fragment up to the next Apa I site, i.e., approximately 4 Kb upstream of the Hind III site. This fragment was inserted into the Sal I site of the pIC vector upstream of the mutated 5 Kb Hind III fragment by blunt ligation.

Since the complete vector contained the chloramphenicol resistance gene, the identification of bacteria carrying the ligated vector was greatly facilitated by selection in the presence of chloramphenicol. The resulting targeting vector is depicted in FIG. 1. This figure also shows the relevant portion of the mouse NPY Y1 gene, as well as the recombined allele obtained after homologous recombination.

Example 2: ES Cells With a Modified NPY Y1 Receptor Allele Produced by Homologous Recombination The targeting vector described in Example 1 was linearized using Sal I and BamHI together, and then introduced by electroporation into HM-1 mouse ES cells (Selfridge et al., *Som. Cell Molec. Genet.* 18:325 (1992)). The cells were then grown in medium containing G418 (400 μg/ml) and gancyclovir (2 μM) to enrich for transformants having the neomycin resistance gene integrated into an endogenous NPY Y1 receptor allele.

DNA was isolated from G418$^r$/GANC$^r$ cell colonies, incubated with restriction enzyme Nco I, and the digestion products separated on an agarose gel. Bands were transferred from the gel to a nitrocellulose membrane, and hybridizations were then performed with the radiolabeled probe depicted in FIG. 1 (see SEQ ID NO:2). The results obtained indicated the presence of a recombined allele in the cells and suggested that 15% of the total colony number contained ES cells with a recombined allele.

Figure 2:
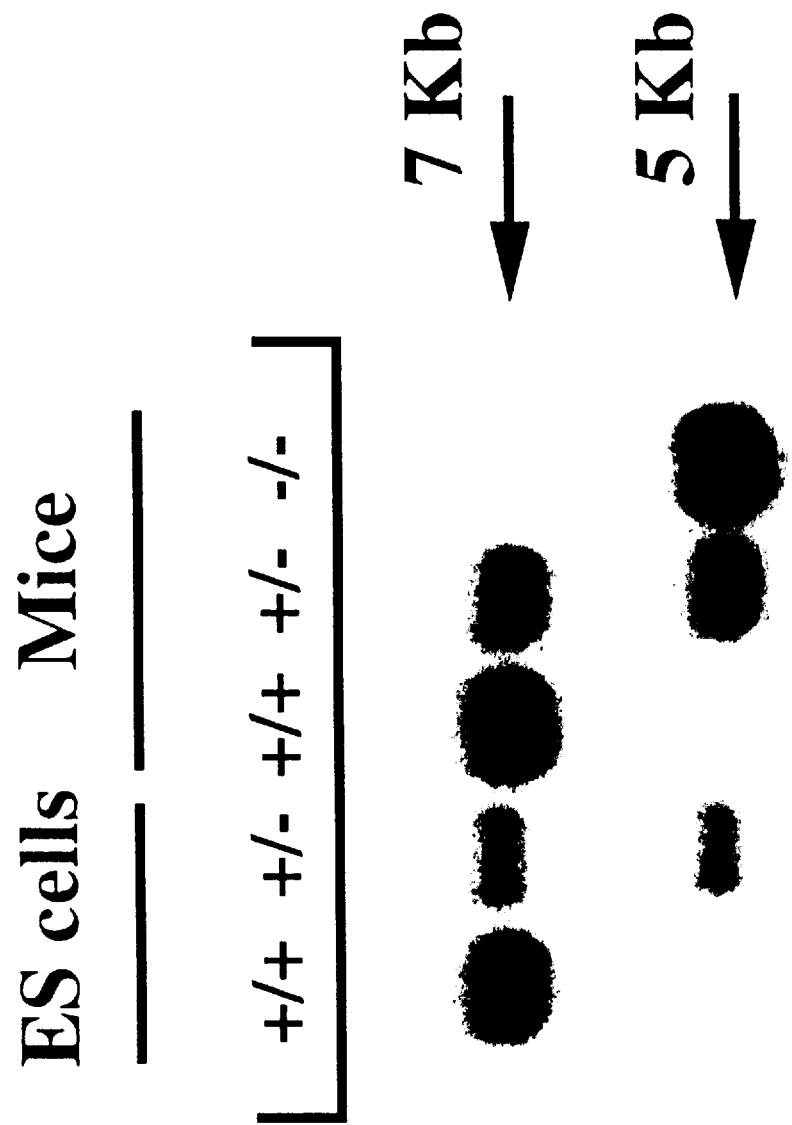
FIG. 2: This figure shows the results of a Southern blot performed on DNA obtained from ES cells containing only wild type NPY Y1 receptor genes (+/+); ES cells heterozygous for the NPY Y1 receptor mutation (+/−); DNA derived from normal mice (+/+); from mice heterozygous for the NPY Y1 receptor mutation (+/−) and from mice homozygous for the NPY Y1 receptor mutation (−/−). In all cases, DNA was digested with Nco I and the probe shown in FIG. 1 was used in hybridizations. The wild type NPY Y1 DNA fragment appears as a band with the molecular weight of about 7 Kb whereas DNA fragments that have undergone mutation by homologous recombination have band positions characteristic of a 5 Kb molecular weight.

FIG. 2 shows a representative Southern blot of DNA from ES cells containing either wild type NPY Y1 receptor alleles (+/+) or one recombined and one wild type allele (+/−). The wild type specific band has an apparent molecular weight of 7 Kb whereas the recombined specific signal has a band size corresponding to a weight of 5 Kb.

Example 3: Transgenic Mice Deficient in the Expression of the NPY Y1 Receptor Gene Male chimeric mice were generated by microinjection of ES cells carrying a recombined allele into C57/B16 mouse blastocysts (3.5 p.c.) and the implantation of these blastocysts into pseudopregnant mice (see, Bradley, et al., *Nature* 309:255 (1984)). One male was found to transmit the ES cell-derived agouti coat color to its offspring at a frequency of 100 percent. Tail DNA was isolated from these offspring and analyzed by Southern blots following incubation with the Nco I restriction enzyme as described above. The blots demonstrated the transmission into the mouse genome of the mutation altering the NPY Y1 receptor allele in transformant ES cells. As can be seen from the results shown in FIG. 2, breeding of the chimeric male mouse and of its heterozygote progeny (+/−) produced mice homozygous for the mutation (−/−).

Example 4: Analysis of Receptor Expression in Transgenic Mice Mutated in Both NPY Y1 Receptor Alleles Total RNA was isolated from different tissues obtained from either a normal mouse or a mouse homozygous for the mutant NPY Y1 receptor allele. The RNA was reverse transcribed and then amplified by PCR in order to detect the presence of Y1 receptor RNA in preparations. GAPDH RNA underwent a similar amplification and was used as a positive control in these experiments. The sequences of the primers used for the amplification of the NPY Y1 receptor and the GAPDH RNA are as follows:

NPY Y1 Receptor Primers:
Forward: 5'-AAA TGT GTC ACT TGC GGC GTT C-3' (SEQ ID NO:3)
Backward: 5'-TGG CTA TGG TCT CGT AGT CAT CGT C-3'(SEQ ID NO:4)
GAPDH Primers:
Forward: 5'-AAG CCC ATC ACC ATC TTC CAG GAG-3' (SEQ ID NO:5)
Backward: 5'-AGC CCT TCC ACA ATG CCA AAG-3' (SEQ ID NO:6)

Figure 3:
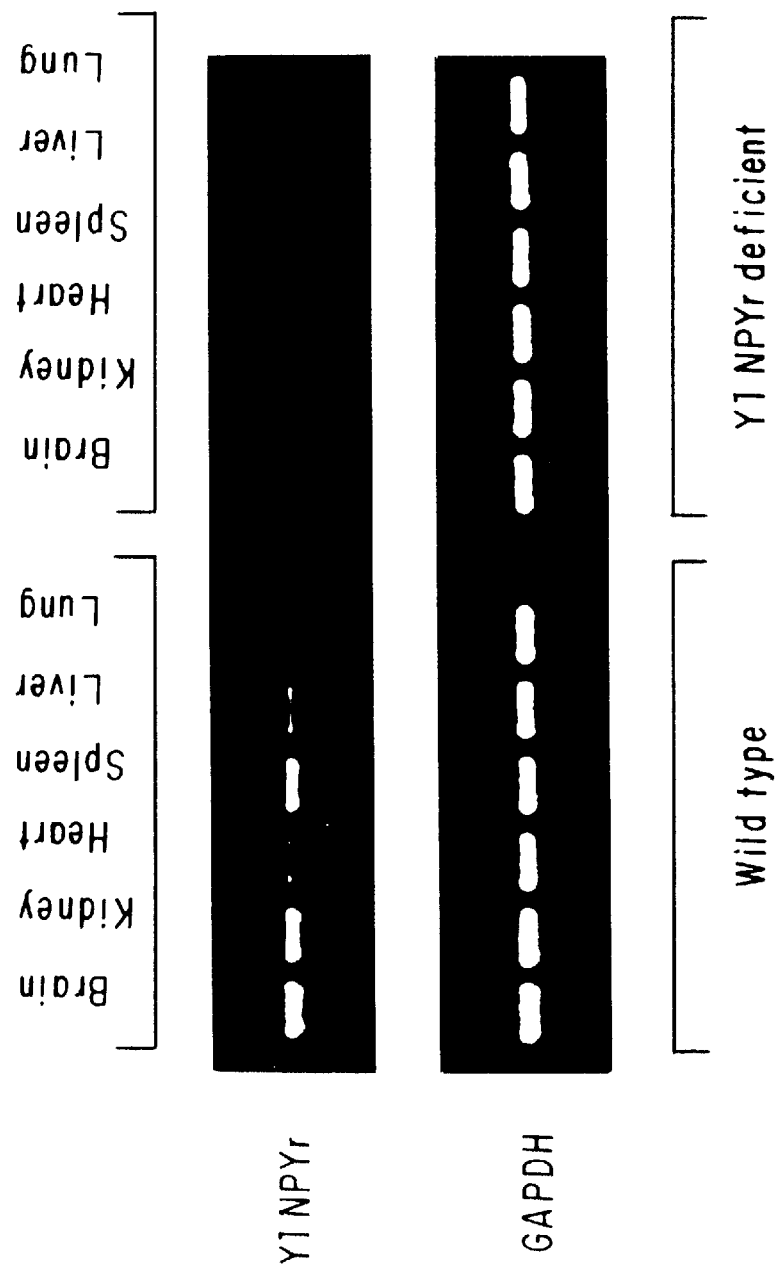
FIG. 3: Total RNA was isolated from a variety of tissues derived from either wild type mice or mice homozygous for the NPY Y1 receptor mutation. The RNA was reverse transcribed and NPY Y1 receptor DNA was then amplified using PCR. Control amplifications were performed on the reverse transcribed RNA preparations for the GAPDH gene. The figure shows consistent amplification of the control gene in all preparations. However, only tissues derived from wild type animals evidence expression of the Y1 receptor.

The results shown in FIG. 3 demonstrate the absence of NPY Y1 receptor expression in tissues from a mouse homozygous for the NPY Y1 receptor gene mutation.

Figure 4:
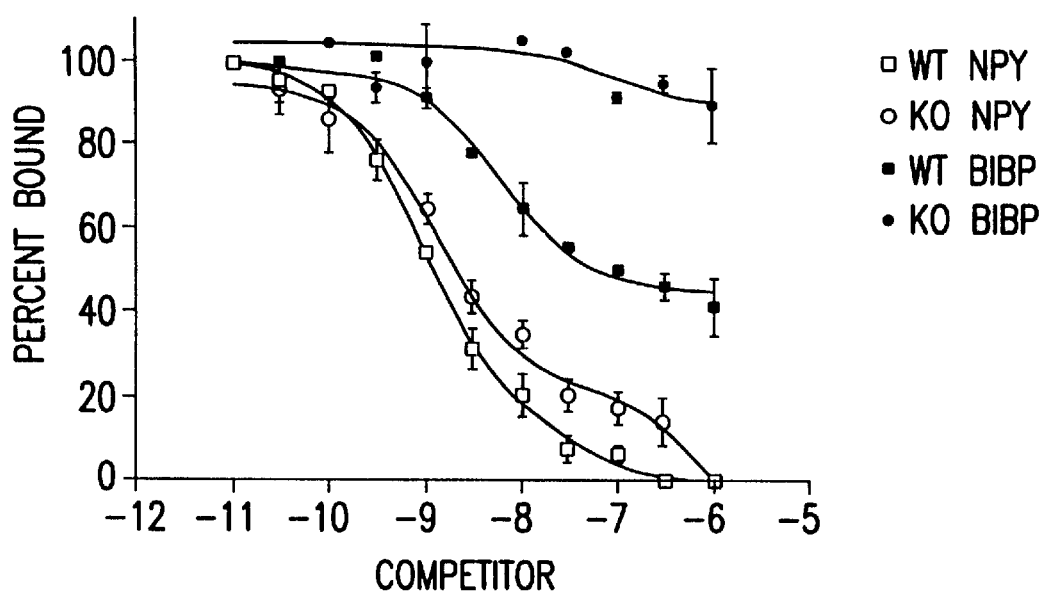
FIG. 4.

Example 5: Competitive Binding Assays Performed Using Tissue Derived from Transgenic Mice Deficient in NPY Y1 Receptor Expression Brain membranes were prepared from either wild type (WT) or NPY Y1 receptor-deficient mice (KO) (for a description of the procedure used for preparing brain membranes, see Martel et al., *Mol. Pharmacol.* 38:494 (1990)). The membranes were incubated in the presence of a constant amount of radiolabeled NPY and increasing concentrations of the highly selective Y1 antagonist, BIBP (Rudolf, et al., Eur J Pharmacol. 271:R11) (1994)). After three hours of incubation, membranes were washed and bound radioactivity was determined using a gamma counter. Nonspecific binding was subtracted from total binding. The data shown in FIG. 4 indicates that BIBP was not able to displace NPY from the membranes of NPY Y1 receptor mutant animals, suggesting the absence of Y1 binding sites.

Example 6: Assay of Response to Drug Administration in Y1 Receptor Deficient Transgenic Animals (Lack of Hypertensive Response)

Changes in blood pressure in response to the administration of NPY was examined in wild type mice (+/+), mice heterozygous for the mutation affecting the NPY Y1 receptor gene (+/−) and homozygous NPY Y1 receptor-mutant mice (−/−) (for a description of assays measuring blood pressure, see Flückiger, et al., *J. Appl. Physiol.* 167:250 (1989), Wiesel et al., *Hypertension,* in press (1997)).

Figure 5:
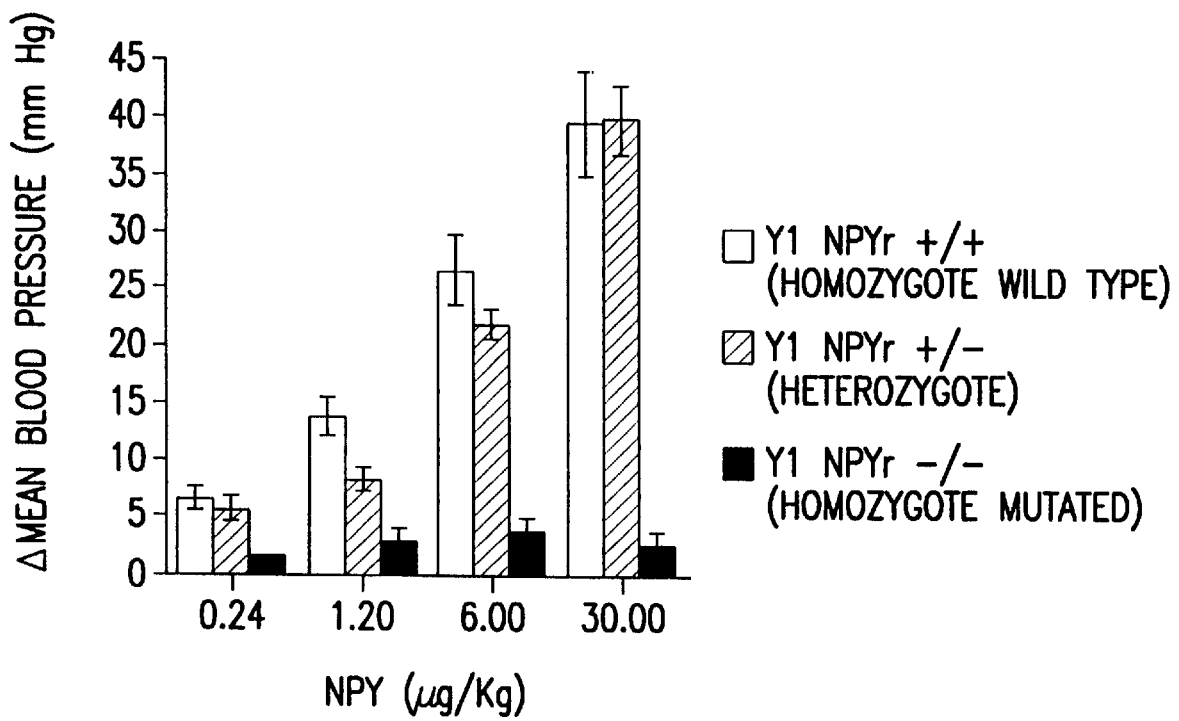
FIG. 5.

The mice were catheterized by inserting a piece of polyethylene tubing in the carotid artery for blood pressure measurement and in the jugular vein for drug infusion. The intraarterial line was connected to a pressure transducer. Various concentrations of drug were then infused through the venous line and changes in blood pressure were determined. The results shown in FIG. 5 demonstrate the absence of a normal pressure response in homozygous mutant animals.

Example 7: Reduction of Food Intake in Y1 Deficient Transgenic Animals

Food intake by wild type (+/+) and homozygous NPY Y1 receptor-deficient mice (−/−) was determined (for a description of the assay, see Campfield, et al., *Science* 269:546 (1995)). Mice were housed in individual cages and deprived of food for 24 hours, from 6 pm until 6 pm the following day. During this time, water was provided ad libitum.

Figure 8:
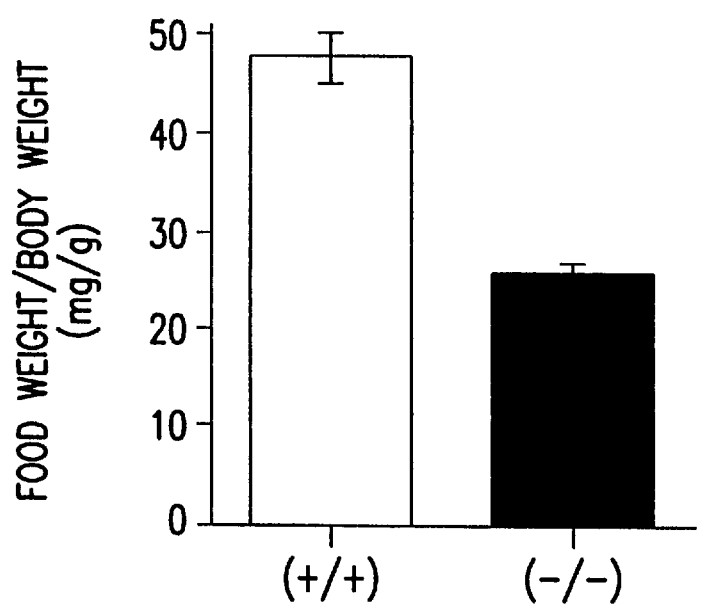
FIG. 8.

Animals were then provided with a pre-weighed amount of food and intake was determined 90 minutes thereafter by weighing the food remaining. The results in FIG. 8 show that NPY Y1 receptor-deficient mice eat less than control littermates in response to starvation. Results are expressed as the amount of food consumed in 90 minutes normalized to body weight.

All references cited herein are fully incorporated by reference. It will be understood by one of skill in the art that the invention may be performed within a wide and equivalent range of conditions, parameters and the like, without affecting the spirit or scope of the invention or any embodiment thereof.

What is claimed is:

1. A DNA construct comprising a disrupted mouse NPY Y1 receptor gene, wherein said disruption is by the insertion of a heterologous marker sequence into said gene such that the protein encoded by said disrupted mouse NPY Y1 receptor gene does not bind NPY.

2. The DNA construct of claim 1, wherein said marker sequence is expressed in said mouse host cell and forms a product that can be used in selecting cells that have undergone homologous recombination.

3. The DNA construct of claim 2, wherein said marker sequence comprises a neomycin resistance gene sequence.

4. The DNA construct of claim 3, wherein said neomycin resistance gene sequence is is inserted into exon 2 of solid NPY Y1 receptor gene.

5. The DNA construct of claim 4, further comprising the HSV-thymidine kinase gene.

6. The DNA construct of claim 1, further comprising a selection sequence that can be used to distinguish between recombinant cells in which recombination has occurred at the NPY Y1 receptor gene site and recombinant cells in which recombination has occurred elsewhere in the genome.

7. The DNA construct of claim 6, wherein said selection sequence comprises the HSV-thymidine kinase gene.

8. A mouse embryonic stem cell comprising the DNA construct of claim 1 integrated into its genome such that the endogenous NPY Y1 receptor gene is disrupted, and wherein the protein encoded by said disrupted mouse NPY Y1 receptor gene does not bind NPY.

9. A method of producing a homozygous transgenic mouse lacking functional NPY Y1 receptors, said method comprising:

a) obtaining a DNA construct comprising a disrupted mouse NPY Y1 receptor gene, wherein said disruption is by the insertion of an heterologous marker sequence;

b) introducing said DNA construct into a mouse ES cell such that the endogenous NPY Y1 receptor gene is disrupted;

c) selecting ES cells comprising said disrupted NPY Y1 receptor allele;

d) incorporating the ES cells of step c) into a mouse embryo;

e) transferring said embryo into a pseudopregnant mouse;

f) developing said embryo into a viable offspring;

g) screening offspring to identify heterozygous mice comprising said disrupted NPY Y1 receptor gene;

h) breeding said heterozygous mice to produce homozygous transgenic mice, wherein the protein encoded by said disrupted mouse NPY Y1 receptor gene does not bind NPY.

10. The method of claim 9, wherein said marker sequence comprises the neomycin resistance gene.

11. The method of claim 10, wherein said DNA construct further comprises the HSV-thymidine kinase gene.

12. The method of claim 10, wherein said neomycin resistance gene is is inserted into exon 2 of said NPY Y1 receptor gene sequence.

13. A homozygous transgenic mouse produced by the method of claim 9, wherein the mouse comprises a disrupted NPY Y1 receptor gene, and wherein the protein encoded by said disrupted mouse NPY Y1 receptor gene does not bind NPY.

14. A homozygous transgenic mouse whose genome comprises a disrupted NPY Y1 gene, and wherein the protein encoded by said disrupted mouse NPY Y1 receptor gene does not bind NPY.

15. The transgenic mouse of claim 14, wherein said disruption is present at the NPY Y1 receptor gene loci in both the somatic and germ cells of said mouse.

16. The transgenic mouse of claim 15, wherein said transgene comprises a neomycin resistance gene.

17. Cells isolated from the transgenic mouse of claim 14, wherein the cells comprise a disrupted NPY Y1 receptor gene, and wherein the protein encoded by said disrupted mouse NPY Y1 receptor gene does not bind NPY.

18. Cell lines comprising cells isolated from the transgenic mouse of claim 14, wherein the cells comprise a disrupted NPY Y1 receptor gene, and wherein the protein encoded by said disrupted mouse NPY Y1 receptor gene does not bind NPY.

19. Tissues isolated from the transgenic mouse of claim 14, wherein the cells of said tissues comprise a disrupted NPY Y1 receptor gene, and wherein the protein encoded by said disrupted mouse NPY Y1 receptor gene does not bind NPY.

20. A method of determining if a compound produces a physiological response in the absence of NPY Y1 receptors that bind NPY, said method comprising:

a) administering said compound to the transgenic mouse of claim 14; and b) assaying said mouse for said physiological response.

21. The method of claim 20 wherein said physiological response is selected from the group consisting of:

(a) a change in blood pressure;

(b) neovascularization;

(c) analgesia;

(d) eating behavior;

(e) a change in body weight;

(f) body temperature;

(g) insulin secretion;

(h) gonadotropin secretion;

(i) anxiety;

(j) nasal secretion;

(k) bronchial secretion;

(l) vasoconstriction;

(m) loss of memory; and (n) stress.

22. A method for assaying a compound for its ability to bind to the NPY Y1 receptor, said method comprising:

a) obtaining a first receptor preparation from the transgenic mouse of claim 14;

b) obtaining a second receptor preparation from a source known to bind neuropeptide Y;

c) incubating said first and second receptor preparations with

I) a ligand known to bind to neuropeptide Y receptors; and ii) said compound; and d) determining the extent of ligand binding displacement by said compound for said first and said second receptor preparations.

23. The method of claim 22, wherein said ligand is detachable labeled neuropeptide Y.

* * * * *